(12) United States Patent
McCarthy et al.

(10) Patent No.: US 7,686,949 B2
(45) Date of Patent: Mar. 30, 2010

(54) HYDROTREATING PROCESS FOR LUBE OIL BOILING RANGE FEEDSTREAMS

(75) Inventors: Stephen J. McCarthy, Center Valley, PA (US); Jean W. Beeckman, Columbia, MD (US); Sylvain S. Hantzer, Purcellville, VA (US); Geoffrey L. Woolery, Flemington, NJ (US); Glenn R. Sweeten, East Stroudsburg, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 1181 days.

(21) Appl. No.: 11/205,606

(22) Filed: Aug. 17, 2005

(65) Prior Publication Data

US 2006/0199986 A1 Sep. 7, 2006

Related U.S. Application Data

(60) Provisional application No. 60/607,803, filed on Sep. 8, 2004.

(51) Int. Cl.
*C07C 5/10* (2006.01)

(52) U.S. Cl. .................. 208/210; 208/208 R; 585/266; 585/269; 502/64; 502/65; 502/66; 502/67; 502/68; 502/69; 502/70; 502/71

(58) Field of Classification Search ................ 585/266, 585/269; 208/106–108, 112, 208 R, 210; 502/64–71
See application file for complete search history.

(56) References Cited

U.S. PATENT DOCUMENTS

| 5,227,353 | A | * | 7/1993 | Apelian et al. ................. 502/74 |
| 5,290,744 | A | * | 3/1994 | Degnan Jr. et al. ............ 502/67 |
| 5,573,657 | A | | 11/1996 | Degnan et al. |
| 5,837,639 | A | | 11/1998 | Kresge et al. |
| 2002/0112989 | A1 | | 8/2002 | Shih et al. |

FOREIGN PATENT DOCUMENTS

WO    WO 94/26846    11/1994

* cited by examiner

*Primary Examiner*—Robert J Hill, Jr.
*Assistant Examiner*—Brian McCaig
(74) *Attorney, Agent, or Firm*—Robert A Migliorini

(57) ABSTRACT

An improved hydrotreating process for use with lube oil boiling range feedstreams utilizing a catalyst comprising a hydrogenation-dehydrogenation component selected from the Group VIII noble metals and mixtures thereof, a mesoporous support, and a binder.

16 Claims, 1 Drawing Sheet

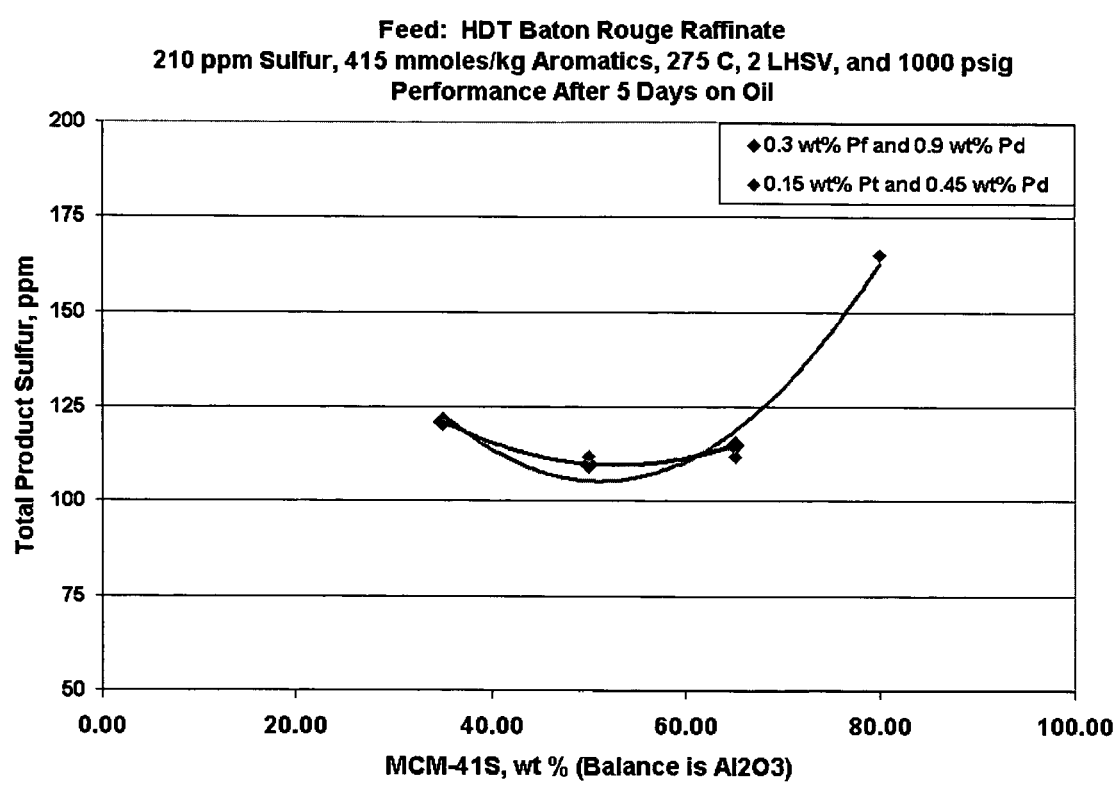
FIGURE

HYDROTREATING PROCESS FOR LUBE OIL BOILING RANGE FEEDSTREAMS

CROSS-REFERENCE TO RELATED APPLICATION

This application claims benefit of U.S. Provisional Patent Application Ser. No. 60/607,803 filed Sep. 8, 2004.

FIELD OF THE INVENTION

This invention relates to a hydrotreating process for lube oil boiling range feedstreams. More particularly, the present invention is directed at a hydrotreating process for lube oil boiling range feedstreams utilizing a catalyst comprising a hydrogenation-dehydrogenation component selected from the Group VIII noble metals and mixtures thereof, a mesoporous support, and a binder.

BACKGROUND OF THE INVENTION

Historically, lubricating oil products for use in applications such as automotive engine oils have used additives to improve specific properties of the basestocks used to prepare the finished products. With the advent of increased environmental concerns, the performance requirements for the basestocks themselves have increased. For example, American Petroleum Institute (API) requirements for Group II basestocks include a saturates content of at least 90%, a sulfur content of 0.03 wt. % or less and a viscosity index (VI) between 80 and 120. Currently, there is a trend in the lube oil market to use higher quality basestocks in order to meet the demand for higher quality products that provide for increased fuel economy, reduced emissions, etc.

Conventional techniques for preparing basestocks such as hydrocracking or solvent extraction require severe operating conditions such as high pressure and temperature or high solvent:oil ratios and high extraction temperatures to reach these higher basestock qualities. Either alternative involves expensive operating conditions and low yields.

Hydrocracking has been combined with hydrotreating as a preliminary step. However, this combination also results in decreased yields of lubricating oils due to the conversion to distillates that typically accompany the hydrocracking process.

In U.S. Pat. No. 5,573,657, a hydrogenation catalyst, and process using the same, is described wherein a mineral oil based lubricant is passed over a mesoporous crystalline material, preferably with a support, containing a hydrogenation metal function. The supported mesoporous material has pore diameters greater than 200 Å. The hydrogenation process is operated such that the product produced therein has a low degree of unstaturation.

However, there is still a need in the art for an effective process to prepare quality lubricating oil basestocks.

SUMMARY OF THE INVENTION

The present invention is directed at a process used to hydrotreat lube oil boiling range feedstreams. The process comprises:
  a) contacting a lube oil boiling range feedstreams containing aromatics and nitrogen and organically bound sulfur contaminants with a hydrotreating catalyst in the presence of a hydrogen-containing treat gas in a reaction stage operated under effective hydrotreating conditions, wherein said hydrotreating catalyst comprises:
    i) about 40 wt. % to less then 60 wt. % of an inorganic, porous, non-layered, crystalline, mesoporous support material;
    ii) 40 to about 60 wt. % of a binder material; and
    iii) at least one hydrogenation-dehydrogenation component selected from the Group VIII noble metals and mixtures thereof.

In one embodiment of the instant invention, the inorganic, porous, non-layered, crystalline, mesoporous support material of the hydrotreating catalyst is characterized as exhibiting an X-ray diffraction pattern with at least one peak at a d-spacing greater than 18 Å. The support material is further characterized as having a benzene absorption capacity greater than 15 grams benzene per 100 grams of the material at 50 torr (6.67 kPa) and 25° C.

In a preferred form, the support material of the hydrotreating catalyst is characterized by a substantially uniform hexagonal honeycomb microstructure with uniform pores having a $d_{100}$ value greater than 18 Å.

In another preferred form, the support material of the hydrotreating catalyst is MCM-41.

In yet another embodiment of the instant invention, the lube oil boiling range feedstream is hydrotreated in a two stage hydrotreating process. The first stage contains a conventional hydrotreating catalyst, and the second reaction stage contains a hydrotreating catalyst comprising a mesoporous support, a binder material, and a hydrogenation-dehydrogenation metal. This embodiment of the instant invention comprises:
  a) contacting a lube oil boiling range feedstream containing aromatics, nitrogen and organically bound sulfur contaminants in a first reaction stage operated under effective hydrotreating conditions and in the presence of hydrogen-containing treat gas with a hydrotreating catalyst comprising about at least one Group VIII metal oxide and at least one Group VI metal oxide thereby producing a reaction product comprising at least a vapor product and a liquid lube oil boiling range product; and
  b) contacting said reaction product with a hydrotreating catalyst in the presence of a hydrogen-containing treat gas in a second reaction stage operated under effective hydrotreating conditions, wherein said hydrotreating catalyst comprises:
    i) about 40 wt. % to less then 60 wt. % of an inorganic, porous, non-layered, crystalline, mesoporous support material;
    ii) 40 to about 60 wt. % of a binder material; and
    iii) at least one hydrogenation-dehydrogenation component selected from the Group VIII noble metals and mixtures thereof.

In another embodiment of the instant invention, the process further comprises:
  a) separating said vapor product from said liquid lube oil boiling range product; and
  b) conducting said liquid lube oil boiling range boiling range product to the second reaction stage containing said hydrogenation catalyst.

BRIEF DESCRIPTION OF THE FIGURE

The FIGURE is a graph depicting the desulfurization performance of catalysts with various binder and support material concentrations versus the time the various catalysts were used in a hydrotreating process.

DETAILED DESCRIPTION OF THE INVENTION

The present invention is a process used to hydrotreating lube oil boiling range feedstreams. In the practice of the present invention, a lube oil boiling range feedstream containing aromatics and nitrogen and organically bound sulfur contaminants is contacted with a hydrotreating catalyst in the presence of a hydrogen-containing treat gas. The hydrotreating catalyst comprises about 40 wt. % to less then 60 wt. % of an inorganic, porous, non-layered, crystalline, mesoporous support material, 40 to about 60 wt. % of a binder material and a hydrogenation-dehydrogenation component. The hydrogenation-dehydrogenation component is selected from the Group VIII noble metals and mixtures thereof. The contacting of the lube oil boiling range feedstream with the hydrotreating catalyst occurs in a reaction stage that is operated under effective hydrotreating conditions.

Feedstreams

Lube oil boiling range feedstreams suitable for use in the present invention include any conventional feedstreams used in lube oil processing. Such feedstreams typically include wax-containing feedstreams such as feeds derived from crude oils, shale oils and tar sands as well as synthetic feeds such as those derived from the Fischer-Tropsch process. Typical wax-containing feedstreams for the preparation of lubricating base oils have initial boiling points of about 315° C. or higher, and include feeds such as reduced crudes, hydrocrackates, raffinates, hydrotreated oils, atmospheric gas oils, vacuum gas oils, coker gas oils, atmospheric and vacuum resids, deasphalted oils, slack waxes and Fischer-Tropsch wax. Such feeds may be derived from distillation towers (atmospheric and vacuum), hydrocrackers, hydrotreaters and solvent extraction units, and may have wax contents of up to 50% or more. Preferred lube oil boiling range feedstreams boil above about 650° F. (343° C.).

Lube oil boiling range feedstreams suitable for use herein also contain aromatics and nitrogen- and sulfur-contaminants. Feedstreams containing up to 0.2 wt. % of nitrogen, based on the feedstream, up to 3.0 wt. % of sulfur, and up to about 50 wt. % aromatics can be used in the present process. It is preferred that the sulfur content of the feedstreams be below about 500 wppm, preferably below about 300 wppm, more preferably below about 200 wppm. Thus, in some instances, the lube oil boiling range feedstream may be hydrotreated with a conventional hydrotreating catalyst prior to contacting the hydrotreating catalyst comprising the mesoporous support. Feeds having a high wax content typically have high viscosity indexes of up to 200 or more. Sulfur and nitrogen contents may be measured by standard ASTM methods D5453 and D4629, respectively.

Support Materials

As stated above, the present invention involves contacting a lube oil boiling range feedstream with a hydrotreating saturation catalyst that comprises about 40 wt. % to less then 60 wt. % of a support material, 40 to about 60 wt. % of a binder material, and a hydrogenation-dehydrogenation component. It is preferred that the hydrotreating catalyst comprise about 45 to 55 wt. % support material, more preferably about 47 to 52 wt. % support material, and most about 48 to 51 wt. % support material.

Support materials suitable for use in the present invention include synthetic compositions of matter comprising an ultra-large pore size crystalline phase. Suitable support materials are inorganic, porous, non-layered crystalline phase materials that are characterized (in its calcined form) by an X-ray diffraction pattern with at least one peak at a d-spacing greater than about 18 Å with a relative intensity of 100. The support materials suitable for use herein are also characterized as having a benzene sorption capacity greater than 15 grams of benzene per 100 grams of the material at 50 torr (6.67 kPa) and 25° C. Preferred support materials are inorganic, porous, non-layered material having a hexagonal arrangement of uniformly-sized pores with a maximum perpendicular cross-section pore dimension of at least about 13 Å, and typically in the range of about 13 Å to about 200 Å. A more preferred support material is identified as MCM-41. MCM-41 has a characteristic structure of hexagonally-arranged, uniformly-sized pores of at least 13 Å diameter, exhibits a hexagonal electron diffraction pattern that can be indexed with a $d_{100}$ value greater than about 18 Å, which corresponds to at least one peak in the X-ray diffraction pattern. MCM-41 is described in U.S. Pat. Nos. 5,098,684 and 5,573,657, which are hereby incorporated by reference, and also, to a lesser degree, below.

The inorganic, non-layered mesoporous crystalline support materials used as components in the hydrotreating catalyst have a composition according to the formula $M_{n/q}(W_aX_bY_cZ_dO_h)$. In this formula, W is a divalent element, selected from divalent first row transition metal, preferably manganese, cobalt, iron, and/or magnesium, more preferably cobalt. X is a trivalent element, preferably aluminum, boron, iron and/or gallium, more preferably aluminum. Y is a tetravalent element such as silicon and/or germanium, preferably silicon. Z is a pentavalent element, such as phosphorus. M is one or more ions, such as, for example, ammonium, Group IA, IIA and VIIB ions, usually hydrogen, sodium and/or fluoride ions. "n" is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1. In a preferred embodiment of support materials suitable for use herein, (a+b+c) is greater than d, and h=2. Another further embodiment is when a and d=0, and h=2. Preferred materials for use in making the support materials suitable for use herein are the aluminosilicates although other metallosilicates may also be used.

In the as-synthesized form, the support materials suitable for use herein have a composition, on an anhydrous basis, expressed empirically by the formula $rRM_{n/q}(W_aX_bY_cZ_dO_h)$, where R is the total organic material not included in M as an ion, and r is the coefficient for R, i.e., the number of moles or mole fraction of R. The M and R components are associated with the material as a result of their presence during crystallization, and are easily removed or, in the case of M, replaced by post-crystallization methods described below. To the extent desired, the original M, e.g., sodium or chloride, ions of the as-synthesized material of this invention can be replaced in accordance with conventional ion-exchange techniques. Preferred replacing ions include metal ions, hydrogen ions, hydrogen precursor, e.g., ammonium, ions and mixtures of these ions. Particularly preferred ions are those which provide the desired metal functionality in the final catalyst. These include hydrogen, rare earth metals and metals of Groups VIIA (e.g., Mn), VIIIA (e.g., Ni), IB (e.g., Cu), IVB (e.g., Sn) of the Periodic Table of the Elements and mixtures of these ions.

The crystalline (i.e., having sufficient order to provide a diffraction pattern such as, for example, by X-ray, electron or neutron diffraction, following calcination with at least one peak) mesoporous support materials are characterized by their structure, which includes extremely large pore windows as well as by its high sorption capacity. The term "mesoporous", as used herein, is meant to indicate crystals having uniform pores within the range of from about 13 Å to about 200 Å. It should be noted that "porous", as used herein, is meant to refer to a material that adsorbs at least 1 gram of a small molecule, such as Ar, $N_2$, n-hexane or cyclohexane, per 100 grams of the porous material.

The support materials suitable for use herein can be distinguished from other porous inorganic solids by the regularity of its large open pores, whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. Thus, support materials for use herein can also be described as having a hexagonal arrangement of large open channels that can be synthesized with open internal diameters from about 13 to about 200 Å, preferably from about 13 to about 100 Å.

The term "hexagonal", as used herein, is intended to encompass not only materials that exhibit mathematically perfect hexagonal symmetry within the limits of experimental measurement, but also those with significant observable deviations from that ideal state. Thus, "hexagonal" as used to describe the support materials suitable for use herein is meant to refer to the fact that most channels in the material would be surrounded by six nearest neighbor channels at roughly the same distance. It should be noted, however, that defects and imperfections in the support material will cause significant numbers of channels to violate this criterion to varying degrees, depending on the quality of the material's preparation. Samples which exhibit as much as ±25% random deviation from the average repeat distance between adjacent channels still clearly give recognizable images of the MCM-41 materials. Comparable variations are also observed in the $d_{100}$ values from the electron diffraction patterns.

The support materials suitable for use herein can be prepared by any means known in the art, and are generally formed by the methods described in U.S. Pat. Nos. 5,098,684 and 5,573,657, which have already been incorporated by reference. Generally, the most regular preparations of the support material give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of suitable support materials show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the suitable support material. The most highly ordered preparations of the suitable support material obtained so far have 20-40 distinct spots observable in the electron diffraction patterns. These patterns can be indexed with the hexagonal hk0 subset of unique reflections of 100, 110, 200, 210, etc., and their symmetry-related reflections.

In its calcined form, support materials suitable for use herein may also be characterized by an X-ray diffraction pattern with at least one peak at a position greater than about 18 Å d-spacing (4.909° 2θ for Cu K-alpha radiation) which corresponds to the $d_{100}$ value of the electron diffraction pattern of the support material. Also, as stated above, suitable support materials display an equilibrium benzene adsorption capacity of greater than about 15 grams benzene/100 grams crystal at 50 torr (6.67 kPa) and 25° C. (basis: crystal material having been treated in an attempt to insure no pore blockage by incidental contaminants, if necessary).

It should be noted that the equilibrium benzene adsorption capacity characteristic of suitable support materials is measured on the basis of no pore blockage by incidental contaminants. For example, the sorption test will be conducted on the crystalline material phase having no pore blockage contaminants and water removed by ordinary methods. Water may be removed by dehydration techniques, e.g., thermal treatment. Pore blocking inorganic amorphous materials, e.g., silica, and organics may be removed by contact with acid or base or other chemical agents such that the detrital material will be removed without detrimental effect on the crystal.

In a more preferred embodiment, the calcined, crystalline, non-layered support materials suitable for use herein can be characterized by an X-ray diffraction pattern with at least two peaks at positions greater than about 10 Å d-spacing (8.842° 2θ for Cu K-alpha radiation) which corresponds to the $d_{100}$ value of the electron diffraction pattern of the support material, at least one of which is at a position greater than about 18 Å d-spacing, and no peaks at positions less than about 10 Å d-spacing with relative intensity greater than about 20% of the strongest peak. Still most preferred, the X-ray diffraction pattern of the calcined material of this invention will have no peaks at positions less than about 10 Å d-spacing with relative intensity greater than about 10% of the strongest peak. In any event, at least one peak in the X-ray diffraction pattern will have a d-spacing that corresponds to the $d_{100}$ value of the electron diffraction pattern of the material.

The calcined, inorganic, non-layered, crystalline support materials suitable for use herein can also be characterized as having a pore size of about 13 Å or greater as measured by physisorption measurements. It should be noted that pore size, as used herein, is to be considered a maximum perpendicular cross-section pore dimension of the crystal.

As stated above, the support materials suitable for use herein can be prepared by any means known in the art, and are generally formed by the methods described in U.S. Pat. Nos. 5,098,684 and 5,573,657, which have already been incorporated by reference. The methods of measuring x-ray diffraction data, equilibrium benzene absorption, and converting materials from ammonium to hydrogen form is known in the art and can also be reviewed in U.S. Pat. No. 5,573,657, which has already been incorporated by reference.

The support materials suitable for use herein can be shaped into a wide variety of particle sizes. Generally speaking, the support material particles can be in the form of a powder, a granule, or a molded product, such as an extrudate having particle size sufficient to pass through a 2 mesh (Tyler) screen and be retained on a 400 mesh (Tyler) screen. In cases where the final catalyst is to be molded, such as by extrusion, the support material particles can be extruded before drying or partially dried and then extruded.

The size of the pores in the present support materials are controlled such that they are large enough that the spatiospecific selectivity with respect to transition state species in reactions such as cracking is minimized (Chen et al., "Shape Selective Catalysis in Industrial Applications", 36 CHEMICAL INDUSTRIES, pgs. 41-61 (1989), to which reference is made for a discussion of the factors affecting shape selectivity). It should also be noted that diffusional limitations are also minimized as a result of the very large pores.

Binder Materials

As stated above, the hydrotreating catalyst used in the present invention also comprises 40 to about 60 wt. % of a binder material. It is preferred that the hydrotreating catalyst comprise about 45 to 55 wt. % binder, more preferably about 47 to 52 wt. % binder, and most about 48 to 51 wt. % binder.

Binder materials suitable for use herein can be selected from any binder material known that is resistant to temperatures and other conditions employed in hydrotreating processes. The support materials are composited with the binder material to form a finished catalyst onto which metals can be added. Binder materials suitable for use herein include active and inactive materials and synthetic or naturally occurring zeolites as well as inorganic materials such as clays and/or oxides such as alumina, silica or silica-alumina. Silica-alumina, alumina and zeolites are preferred binder materials, and alumina is a more binder support material. Silica-alumina may be either naturally occurring or in the form of gelatinous precipitates or gels including mixtures of silica and metal oxides. It should be noted that the inventors herewith recognize that the use of a material in conjunction with a zeolite binder material, i.e., combined therewith or present during its synthesis, which itself is catalytically active may change the conversion and/or selectivity of the finished catalyst. The inventors herewith likewise recognize that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst.

Hydrogenation-Dehydrogenation Component

As stated above, the hydrotreating catalyst used in the present invention further comprises a hydrogenation-dehydrogenation component selected from Group VIII noble metals and mixtures thereof. It is preferred that the hydrogenation-dehydrogenation component be selected from palladium, platinum, rhodium, iridium, and mixtures thereof, more preferably platinum, palladium, and mixtures thereof. It is most preferred that the hydrogenation-dehydrogenation component be platinum and palladium.

The hydrogenation-dehydrogenation component is typically present in an amount ranging from about 0.1 to about 2.0 wt. %, preferably from about 0.2 to about 1.8 wt. %, more preferably 0.3 to about 1.6 wt. %, and most preferably 0.4 to about 1.4 wt. %. All metals weight percents are on support. All metals weight percents are on support. By "on support" we mean that the percents are based on the weight of the support, i.e., the composited support material and binder material. For example, if the support were to weigh 100 grams then 20 wt. % hydrogenation-dehydrogenation component would mean that 20 grams of the hydrogenation-dehydrogenation metal was on the support.

The hydrogenation-dehydrogenation component can be exchanged onto the support material, impregnated into it or physically admixed with it. It is preferred that the hydrogenation/dehydrogenation component be incorporated by impregnation. If the hydrogenation-dehydrogenation component is to be impregnated into or exchanged onto the composited support material and binder, it may be done, for example, by treating the composite with a suitable ion containing the hydrogenation-dehydrogenation component. If the hydrogenation-dehydrogenation component is platinum, suitable platinum compounds include chloroplatinic acid, platinous chloride and various compounds containing the platinum amine complex. The hydrogenation-dehydrogenation component may also be incorporated into, onto, or with the composited support and binder material by utilizing a compound (s) wherein the hydrogenation-dehydrogenation component is present in the cation of the compound and/or compounds or in which it is present in the anion of the compound(s). It should be noted that both cationic and anionic compounds can be used. Non-limiting examples of suitable palladium or platinum compounds in which the metal is in the form of a cation or cationic complex are $Pd(NH_3)_4Cl_2$ or $Pt(NH_3)_4Cl_2$ are particularly useful, as are anionic complexes such as the vanadate and metatungstate ions. Cationic forms of other metals are also very useful since they may be exchanged onto the crystalline material or impregnated into it.

Process

The inventors hereof have unexpectedly found that by using a hydrotreating catalyst comprising the above described amounts of support material, binder material, and hydrogenation-dehydrogenation components, the present invention is more effective at removing sulfur and nitrogen contaminants present in lube oil boiling range feedstreams. Thus, the term "hydrotreating" as used herein refers to processes wherein a hydrogen-containing treat gas is used in the presence of a suitable catalyst that is primarily active for the removal of heteroatoms, such as sulfur, and nitrogen.

Thus, in the practice of the present invention, a lube oil boiling range feedstream as described above is contacted with a hydrotreating as described above under effective hydrotreating conditions. Effective hydrotreating conditions are to be considered those conditions under which at least a portion of the sulfur contaminants present in the lube oil boiling range feedstream are removed or converted. Typical effective hydrotreating conditions include temperatures ranging from about 150° C. to about 425° C., preferably about 200° C. to about 370° C., more preferably about 230° C. to about 350° C. Typical weight hourly space velocities ("WHSV") range from about 0.1 to about 20 $hr^{-1}$, preferably from about 0.5 to about 5 $hr^{-1}$. Any effective pressure can be utilized, and pressures typically range from about 4 to about 70 atmospheres (405 to 7093 kPa), preferably 10 to 40 atmospheres (1013 to 4053 kPa).

In one embodiment of the instant invention, the effective hydrotreating conditions for use with the catalyst comprising the an inorganic, porous, non-layered, crystalline, mesoporous support material are conditions effective at removing at least a portion of the nitrogen and organically bound sulfur contaminants and hydrogenating at least a portion of the aromatics present in the lube oil boiling range feedstream. Hydrotreating under these conditions produces at least a liquid lube oil boiling range product having a lower concentration of aromatics and nitrogen and organically bound sulfur contaminants than the lube oil boiling range feedstream.

As stated above, in some instances, the lube oil boiling range feedstream is first hydrotreated with a conventional hydrotreating catalyst to reduce the sulfur contaminants in the lube oil boiling range feedstream to below about 500 wppm, preferably below about 300 wppm, more preferably below about 200 wppm. In this embodiment, the present process comprises at least two reaction stages, the first containing a conventional hydrotreating catalyst operated under effective hydrotreating conditions, and the second containing an hydrotreating catalyst as described above operated under effective hydrotreating conditions as described above. Therefore, in this embodiment, the lube oil boiling range feedstream is first contacted with a conventional hydrotreating catalyst in the presence of a hydrogen-containing treat gas in a first reaction stage operated under effective hydrotreating conditions in order to reduce the sulfur content of the lube oil boiling range feedstream to within the above-described range. Suitable hydrotreating catalysts for use in the present invention are any conventional hydrotreating catalyst. Conventional hydrotreating catalyst, as used herein, refers to those hydrotreating catalyst which are comprised of at least one Group VIII metal, preferably Fe, Co and Ni, more preferably Co and/or Ni, and most preferably Co; and at least one Group VI metal, preferably Mo and W, more preferably Mo, on a high surface area support material, preferably alumina. It is within the scope of the present invention that more than one type of hydrotreating catalyst be used in the same reaction vessel. The Group VIII metal is typically present in an amount ranging from about 2 to 20 wt. %, preferably from about 4 to 12%. The Group VI metal will typically be present in an amount ranging from about 5 to 50 wt. %, preferably from about 10 to 40 wt. %, and more preferably from about 20 to 30 wt. %. All metals weight percents are on support. By "on support" we mean that the percents are based on the weight of the support. For example, if the support were to weigh 100 grams, then 20 wt. % Group VIII metal would mean that 20 grams of Group VIII metal was on the support.

Effective hydrotreating conditions in the second reaction stage are to be considered those conditions that can effectively reduce the sulfur content of the lube oil boiling range feedstream to within the above-described ranges. These hydrotreating conditions are any of those described above, i.e., temperatures ranging from about 150° C. to about 425° C., preferably about 200° C. to about 370° C., more preferably about 230° C. to about 350° C. Typical weight hourly space velocities ("WHSV") range from about 0.1 to about 20 hr$^{-1}$, preferably from about 0.5 to about 5 hr$^{-1}$, etc. In a preferred embodiment, the effective hydrotreating conditions in the second reaction stage are also conditions effective at removing at least a portion of said organically bound sulfur contaminants and hydrogenating at least a portion of said aromatics.

The contacting of the lube oil boiling range feedstream with the conventional hydrotreating catalyst produces a reaction product comprising at least a vapor product and a liquid lube oil boiling range product. The vapor product typically comprises gaseous reaction products such as H$_2$S, and the liquid reaction product typically comprises a liquid lube oil boiling range product having a reduced level of nitrogen and sulfur contaminants. The reaction product can be passed directly into the second reaction stage, but it is preferred that the gaseous and liquid reaction products be separated, and the liquid reaction product conducted to the second reaction stage. Thus, in one embodiment of the present invention, the vapor product and the liquid lube oil boiling range product are separated, and the liquid lube oil boiling range product conducted to the second reaction stage. The method of separating the vapor product from the liquid lube oil boiling range product is not critical to the instant invention and can be accomplished by any means known to be effective at separating gaseous and liquid reaction products. For example, a stripping tower or reaction zone can be used to separate the vapor product from the liquid lube oil boiling range product. The liquid lube oil boiling range product thus conducted to the second reaction stage will have a sulfur concentration within below about 500 wppm, preferably below about 300 wppm, more preferably below about 200 wppm.

The above description is directed to preferred embodiments of the present invention. Those skilled in the art will recognize that other embodiments that are equally effective could be devised for carrying out the spirit of this invention.

The following example will illustrate the improved effectiveness of the present invention, but is not meant to limit the present invention in any fashion.

EXAMPLE

A series of catalysts were made using MCM-41 mesoporous materials with different ratios of MCM-41 and alumina. MCM-41 mesoporous material was prepared into a filter-cake and this filter-cake was pre-calcined in nitrogen at about 540° C. The pre-calcined MCM-41 solids were then mulled with a Versal-300 alumina binder and extruded into 1/16 inch (1.6 mm) cylinders. The MCM-41 content of the muller mix was varied to 35, 50, and 65 wt. %, on a solids basis. The extrudates were dried and then calcined in air at about 538° C. The calcined extrudates were then co-impregnated with 0.3 wt. platinum, 0.9 wt. palladium. The catalysts then received a final calcination in air at 304° C. to decompose the platinum and palladium compounds. Properties of the finished catalysts are summarized in Table 1 below.

In order to determine the activity of the various catalysts used in the Examples herein, each was separately subjected to the Benzene Hydrogenation Activity ("BHA"). The BHA test is a measure of the activity of the catalyst, and the higher the BHA index, the more active the catalyst. Thus, the performance of each catalyst was screened for hydrogenation activity using the BHA test. The BHA test was performed on each catalyst sample by drying 0.2 grams of the catalyst in helium for one hour at 100° C., then reducing the sample at a selected temperature (120° C. to 350° C., nominally 250° C.) for one hour in flowing hydrogen. The catalyst was then cooled to 50° C. in hydrogen, and the rate of benzene hydrogenation measured at 50° C., 75° C., 100° C., and 125° C. In the BHA test, hydrogen is flowed at 200 sccm and passed through a benzene sparger held at 10° C. The data are fit to a zero-order Arrhenius plot, and the rate constant in moles of product per mole of metal per hour at 100° C. is reported. It should be noted that Pt, Pd, Ni, Au, Pt/Sn, and coked and regenerated versions of these catalysts can be tested also. The pressure used during the BHA test is atmospheric. The results of the BHA test were recorded, and are included in Table 1 below.

TABLE 1

| Catalyst Description | Pt (wt. %) | Pd (wt. %) | Benzene Hydrogenation Activity Index | Oxygen Chemisorption (O/M) |
|---|---|---|---|---|
| 65% MCM-41/ 35% Al$_2$O$_3$ | 0.27 | 0.89 | 607 | 0.65 |
| 50% MCM-41/ 50% Al$_2$O$_3$ | 0.28 | 0.82 | 520 | 0.59 |
| 35% MCM-41/ 65% Al$_2$O$_3$ | 0.27 | 0.83 | 470 | 0.64 |

A second series of were also made using MCM-41 mesoporous materials with different ratios of MCM-41 and alumina. Again, MCM-41 mesoporous material was prepared into a filter-cake and this filter-cake was pre-calcined in nitrogen at about 540° C. The pre-calcined MCM-41 solids were then mulled with a Versal-300 alumina binder and extruded into 1/16 inch (1.6 mm) cylinders. The MCM-41 content of the muller mix was varied to 35, 50, 65 and 80 wt. %, on a solids basis. The extrudates were dried and then calcined in air at about 538° C. The calcined extrudates were then co-impregnated with 0.15 wt. platinum, 0.45 wt. palladium. The catalysts then received a final calcination in air at 304° C. to decompose the platinum and palladium compounds. Properties of these finished catalysts are summarized in Table 2 below.

TABLE 2

| Catalyst Description | Pt (wt. %) | Pd (wt. %) | Benzene Hydrogenation Activity Index | Oxygen Chemisorption (O/M) |
|---|---|---|---|---|
| 65% MCM-41/ 35% Al$_2$O$_3$ | 0.14 | 0.45 | 600 | 0.67 |
| 50% MCM-41/ 50% Al$_2$O$_3$ | 0.14 | 0.41 | 565 | 0.53 |
| 80% MCM-41/ 20% Al$_2$O$_3$ | 0.14 | 0.43 | 870 | 0.49 |
| 35% MCM-41/ 65% Al$_2$O$_3$ | 0.14 | 0.42 | 465 | 0.62 |

After each catalyst was prepared, the performance of each catalyst was separately evaluated for hydrofinishing a hydrotreated 600N dewaxed oil. The dewaxed oil was first hydrotreated to reduce the sulfur content to about 200 wppm. The 600N dewaxed oil had an aromatics concentration of about 415 mmol/kg. Approximately 5 cc of each catalyst was separately loaded into an upflow micro-reactor. About 3 cc of 80-120 mesh sand was added to the catalyst loading to ensure uniform liquid flow. After pressure testing with nitrogen and hydrogen, the catalysts were dried in nitrogen at 260° C. for about 3 hours, cooled to room temperature, activated in hydrogen at about 260° C. for 8 hours and then cooled to 150° C. The 600N dewaxed oil feed was then introduced and operating conditions were adjusted to 2 LHSV, 1000 psig (6996 kPa), and 2500 scf H$_2$/bbl (445 m$^3$/m$^3$). Reactor temperature was increased to 275° C. and then held constant for about 7 to 10 days. Hydrogen purity was 100% and no gas recycle was used.

Product quality as defined by aromatics, sulfur, hydrogen, and nitrogen contents was monitored daily. Total sulfur content as a function of time on stream are shown in the FIGURE herein for the catalysts made using MCM-41 as described in Tables 1 and 2 above. As can be seen in the FIGURE herein, the inventors hereof have unexpectedly found that catalysts made using a 50 wt. % MCM-41 and 50 wt. % alumina provided the highest level of desulfurization.

It should be noted that although Tables 1 and 2 indicate by the BHA test that catalysts having a ratio of MCM-41 and alumina different from the optimal 50:50 ratio discovered by the inventors hereof are more active, the inventors hereof attribute this discrepancy to sulfur in the feed. The BHA test is performed without sulfur present, and the real feed had sulfur present, as described above. Thus, in applications utilizing "real feeds", i.e., feeds that are used in petroleum and/or chemical based processing schemes, a catalyst comprising 50 wt. % MCM-41 and 50 wt. % alumina will provide the highest level of desulfurization.

The invention claimed is:

1. An aromatics saturation process for lube oil boiling range feedstreams comprising:
   a) contacting a lube oil boiling range feedstream containing aromatics, nitrogen and organically bound sulfur contaminants in a first reaction stage operated under effective hydrotreating conditions and in the presence of hydrogen-containing treat gas with a conventional hydrotreating catalyst comprising about at least one Group VIII metal oxide and at least one Group VI metal oxide thereby producing a reaction product comprising at least a vapor product and a liquid lube oil boiling range product; and
   b) contacting said reaction product with a second hydrotreating catalyst in the presence of a hydrogen-containing treat gas in a second reaction stage operated under effective hydrotreating conditions, wherein said second hydrotreating catalyst consisting essentially of:
      i) about 45 wt. % to about 55 wt. % of an inorganic, porous, non-layered, crystalline, mesoporous support material;
      ii) about 45 to about 55 wt % of a binder material; and
      iii) a hydrogenation-dehydrogenation component selected from the Group VIII noble metals and mixtures thereof.

2. The process according to claim 1 wherein said support material is composited with said binder material.

3. The process according to claim 2 wherein the support material has an X-ray diffraction pattern with at least two peaks at positions greater than about 10 Å d-spacing (8.84°2θ for Cu K-alpha radiation) which corresponds to the d$_{100}$ value of the electron diffraction pattern of the support material, at least one of which is at a position greater than about 18 Å d-spacing, and no peaks at positions less than about 10 Å d-spacing with relative intensity greater than about 20% of the strongest peak.

4. The process according to claim 2 wherein the support material has an X-ray diffraction pattern with at least one peak at a position greater than about 18 Å d-spacing (4.990°2θ for Cu K-alpha radiation) which corresponds to the d$_{100}$ value of the electron diffraction pattern of the support material and with no peaks at positions less than about 10 Å d-spacing with relative intensity greater than about 10% of the strongest peak.

5. The process according to claim 2 wherein said hydrogenation-dehydrogenation component is present in an amount ranging from about 0.1 to about 2.0 wt. %.

6. The process according to claim 5 wherein said hydrogenation-dehydrogenation component is selected from palladium, platinum, rhodium, iridium, and mixtures thereof.

7. The process according to claim 2 wherein said lube oil boiling range feedstream is derived from crude oils, shale oils and tar sands as well as synthetic feeds and is selected from lube oil boiling range feedstreams having an initial boiling points of about 315° C. or higher.

8. The process according to claim 7 wherein said lube oil boiling range feedstream contains up to 0.2 wt. % of nitrogen, up to 3.0 wt. % of sulfur, and up to 50 wt. % aromatics, all based on the lube oil boiling range feedstream.

9. The process according to claim 7 wherein said liquid lube oil boiling range product has a sulfur content below about 500 wppm.

10. The process according to claim 9 wherein said process further comprises:
    a) separating said vapor product from said liquid lube oil boiling range product; and
    b) conducting said liquid lube oil boiling range product to the second reaction stage containing said aromatics saturation catalyst.

11. The process according to claim 2 wherein said effective hydrotreating conditions in the second reaction stage are conditions effective at removing at least a portion of said organically bound sulfur contaminants and saturating at least a portion of said aromatics present in said lube oil boiling range feedstream.

12. The process according to claim 11 wherein said effective hydrotreating conditions in the first reaction stage are conditions effective at removing at least a portion of said organically bound sulfur contaminants and saturating at least a portion of said aromatics present in said lube oil boiling range feedstream.

13. The process according to claim 1 wherein said binder material is alumina.

14. The process according to claim 1 wherein the support material displays an equilibrium benzene adsorption capacity of greater than about 15 grams benzene/100 grams crystal at 50 torr (6.67 kPa) and 25° C.

15. The process according to claim 1 wherein said binder material is MCM-41.

16. The process according to claim 15 wherein the hydrogenation-dehydrogenation component is platinum and palladium.

* * * * *